United States Patent [19]

Clement et al.

[11] Patent Number: 5,338,292

[45] Date of Patent: Aug. 16, 1994

[54] DISPOSABLE LAVAGE WITH INSTRUMENT SHIELD

[75] Inventors: Thomas P. Clement; David P. Weber, both of Bloomington, Ind.

[73] Assignee: Mectra Labs, Inc., Bloomfield, Ind.

[21] Appl. No.: 986,272

[22] Filed: Dec. 7, 1992

Related U.S. Application Data

[60] Division of Ser. No. 948,342, Sep. 21, 1992, which is a continuation of Ser. No. 580,945, Sep. 11, 1990, abandoned, which is a continuation-in-part of Ser. No. 432,084, Nov. 6, 1989, Pat. No. 5,019,054.

[51] Int. Cl.$^5$ .................. A61B 17/20; A61B 17/32
[52] U.S. Cl. .......................... 604/22; 606/172
[58] Field of Search .................. 606/167, 172, 190; 604/22, 30, 32, 33, 35, 117, 283

[56] References Cited

U.S. PATENT DOCUMENTS

| | | |
|---|---|---|
| 786,215 | 3/1905 | Hepnar . |
| 1,658,754 | 2/1928 | Wood . |
| 2,437,329 | 3/1948 | Moore . |
| 2,715,899 | 8/1955 | MacLean . |
| 2,812,765 | 11/1957 | Tofflemire . |
| 3,012,752 | 12/1961 | Buck . |
| 3,048,192 | 8/1962 | Murphy, Jr. . |
| 3,081,770 | 3/1963 | Hunter . |
| 3,157,201 | 11/1964 | Littmann . |
| 3,434,691 | 3/1969 | Hamilton . |
| 3,682,177 | 8/1972 | Ames et al. .......... 606/172 |
| 3,783,900 | 1/1974 | Waldbillig . |
| 3,794,032 | 2/1974 | Derouineau . |
| 3,833,000 | 9/1974 | Bridgman . |
| 3,834,372 | 9/1974 | Turney . |
| 4,043,322 | 8/1977 | Robinson . |
| 4,079,737 | 3/1978 | Miller . |
| 4,230,128 | 10/1980 | Aramayo . |
| 4,280,498 | 7/1981 | Jensen . |
| 4,282,873 | 8/1981 | Roth . |
| 4,397,335 | 8/1983 | Doblar et al. . |
| 4,444,184 | 4/1984 | Oretorp .............. 606/167 X |
| 4,552,146 | 11/1985 | Jensen et al. . |
| 4,553,964 | 11/1985 | Sasaki . |
| 4,566,480 | 1/1986 | Parham . |
| 4,581,014 | 4/1986 | Millerd et al. . |
| 4,593,717 | 6/1986 | Levasseur . |
| 4,605,396 | 8/1986 | Tseo et al. . |
| 4,642,097 | 2/1987 | Siposs . |
| 4,648,868 | 3/1987 | Hardwick et al. . |

(List continued on next page.)

FOREIGN PATENT DOCUMENTS 0350291 1/1990 European Pat. Off. .......... 606/172

OTHER PUBLICATIONS

Papacristou, D. N. et al., Resection of the Liver with a Water Jet, Br. J. Surg. vol. 69 (1982), 93–94.
Storz The World of Endoscopy, Semm Instruments for Operative Pelviscopy, 4th Edition, Mar. 1987, pp. 1–4.
K. Semm, "Pelviscopy–operative guidelines", Kiel, Germany, 1988, pp. 53–54.
American Surgical Instruments, Inc., "Nezhat-Dorsey (List continued on next page.)

Primary Examiner—John D. Yasko
Assistant Examiner—Adam J. Cermak
Attorney, Agent, or Firm—Barnes & Thornburg

[57] ABSTRACT

A surgical device has a first cannula formed to define a first interior channel and a second cannula positioned substantially within the first interior channel of the first cannula, The second cannula is formed to define a second interior channel, Both the first cannula and the second cannula are attached to a conduit piece that defines a first passageway in fluid communication with the first interior channel of the first cannula and a second passageway in fluid communication with the second interior channel of the second cannula, A third passageway defined by the conduit piece is in fluid communication with the first interior channel of the first cannula, The second passageway is covered by a breachable seal that permits insertion of instruments therethrough while limiting undesired fluid flow. A knife blade can be attached to said first cannula and said second cannula can be positioned around the knife blade to shield the knife blade.

36 Claims, 4 Drawing Sheets

U.S. PATENT DOCUMENTS

| | | |
|---|---|---|
| 4,654,027 | 3/1987 | Dragan et al. |
| 4,674,500 | 6/1987 | DeSatnick ............ 604/22 X |
| 4,758,235 | 7/1988 | Tu. |
| 4,793,359 | 12/1988 | Sharrow. |
| 4,900,300 | 2/1990 | Lee ............ 604/22 |
| 4,994,067 | 2/1991 | Summers ............ 606/159 |
| 4,994,079 | 2/1991 | Genese et al. ............ 606/206 |
| 5,019,035 | 5/1991 | Missirlian et al. ............ 604/22 |
| 5,106,364 | 4/1992 | Hayfuji et al. ............ 604/22 |

OTHER PUBLICATIONS

Disposable Hydro–Dissection Trumpet Valve", 3 Sheets, Mar. 19, 1990.

Pentax Precision Instrument Corp., "Gastrofiberscope", Surgical Products, Mar. 1990, vol. 9, No. 5, p. 33.

Storz, "Laparoscopic Cholecystectomy for the General Surgeon–Its Time has Come", Surgical Products, May 1990, vol. 9, No. 6, p. 13.

Pentax Precision Instrument Corp., "GI Fiberscopes", Surgical Products, May 1990, vol. 9, No. 6, p. 13.

Richard Wolf, "The Complete Endoscopy Manufacturer", Surgical Products, May 1990. vol. 9, No. 6, p. 20.

Johnson & Johnson Medical Inc., "CIDEX is safe for scopes. Don't take our word for it.", Surgical Products, May 1990, vol. 9, No. 6, p. 25.

Pentax ®, "Pentax ® PNELL Bronchofiberscopes", Surgical Products, May 1990, vol. 9, No. 6, p. 44.

Pentax Precision Instrument Corp., "Therapeutic Gastrofiberscope with Water Jet", Sep. 1990, vol. 10, No. 1, p. 39.

Cabot Medical, "Suction/Irrigation Probe", Surgical Products, Nov. 1990, vol. 10, No. 11, p. 29.

EndoDynamics, Inc., "Aspiration Device", Surgical Products, Nov. 1990, vol. 10, No. 11, p. 30.

Cabot Medical, "Laparoscopic Cholecystectomy From the Company Who Knows Laparoscopy", Surgical Products, Jan. 1991, vol. 10, No. 3, p. 4.

Olympus, "The Olympus Laparoscopic Cholecsytectomy System: Resolution for Gallstones, with the Leader in High-Resolution Optics", Surgical Products, Jan. 1990, vol. 10, No. 3, p. 8.

Apple Medical, "Hunt/Reich Secondary Cannula", Surgical Products, May 1991, vol. 10, No. 7, p. 5.

Baxter Healthcare Corp., "Infusion Pump", Surgical Products, Jun. 1991, vol. 10, No. 8, p. 32.

Core Dynamics TM Inc., "Disposable Trocar with Reusable Cannula", Surgical Products, Jun. 1991, vol. 10, No. 8, p. 4.

"PAL TM", Surgical Products, Jun. 1991, vol. 10, No. 8, p. 37.

Karl Storz, "Laparoscopic Cholecystectomy", p. 1, date unknown.

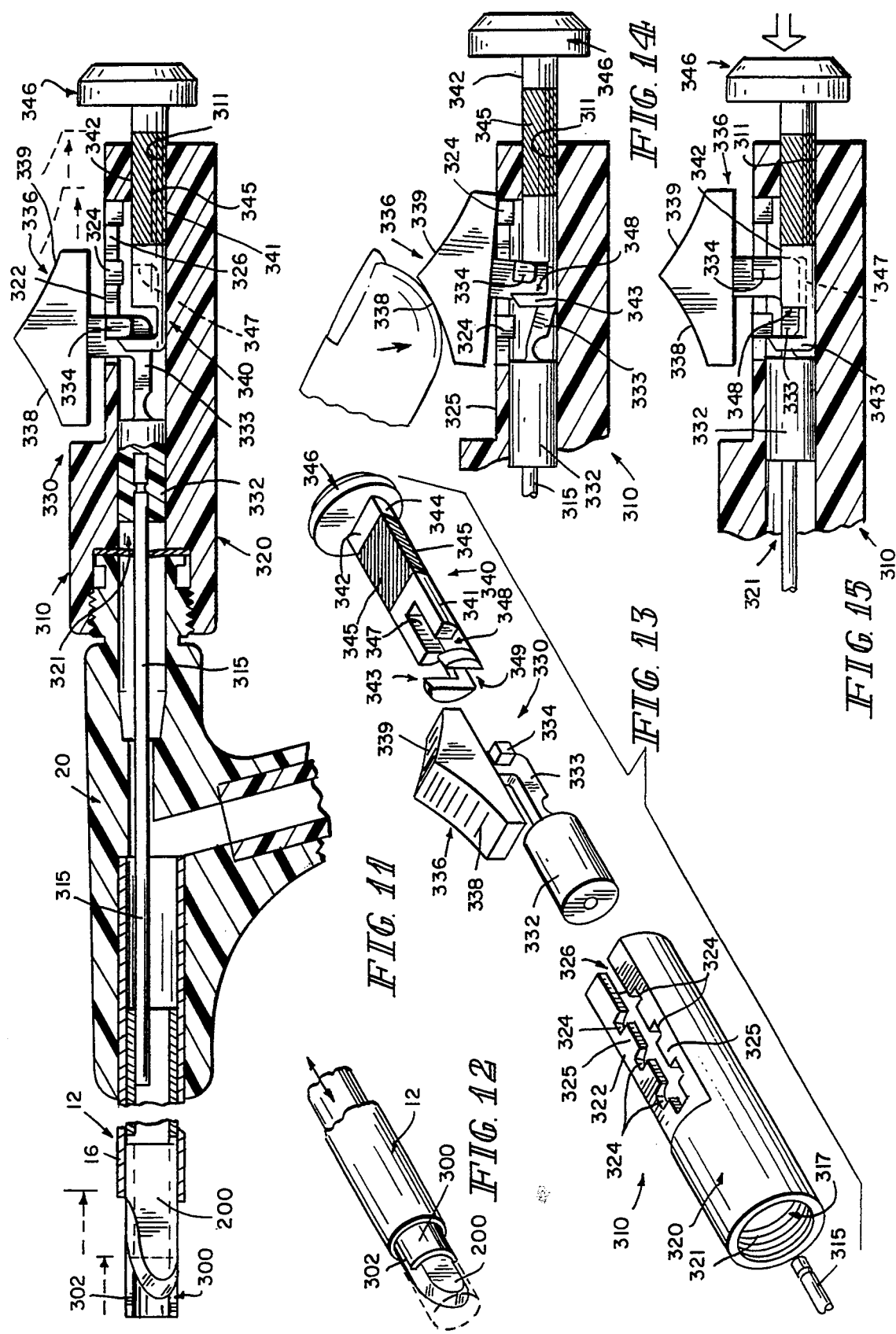

DISPOSABLE LAVAGE WITH INSTRUMENT SHIELD

This is a division of application Ser. No. 07/948,342 filed Sep. 21, 1992, which is a continuation of application Ser. No. 07/580,945 filed Sep. 11, 1990 (now abandoned), which is a continuation-in-part application of application Ser. No. 07/432,084 filed Nov. 6, 1989, now U.S. Pat. No. 5,019,054 issued May 28, 1991.

BACKGROUND AND SUMMARY OF THE INVENTION

The present invention relates to handheld lavages and more particularly to the provision of handheld lavages which may be held securely in one hand and provide irrigation, aspiration, or other therapeutic functions.

Many surgical procedures require instruments capable of cauterizing, slicing, cutting, or otherwise dissecting bodily tissue. However, use of such instruments generally results in the production of blood and other tissue debris in the area of operation of the instrument, obscuring the view of the surgeon and making further cutting or cauterization dangerous. Washing the blood or tissue debris from the area of operation by irrigation with a saline solution, or removing disassociated tissue with an aspiration device are two methods commonly employed by surgeons to clear blood and tissue debris from the operating area. Typically, cutting or cauterizing tissue is accomplished with one instrument, followed by aspiration or irrigation of the cut or cauterized area with a second instrument. The surgeon alternates between use of the two instruments until the operation is complete.

An example of an instrument that provides both irrigation and aspiration is described in U.S. Pat. No. 4,553,957 to Williams et al. A cylindrical tube that acts as a handle conducts fluid through its interior to peripheral outlets in an outer irrigation cannula. Fluid or tissue is removed from the cutting site through an aspiration cannula extending completely through the handle. However, use of this type of instrument can be cumbersome in many surgical operations, because it either requires additional persons to manipulate the aspiration-/irrigation device, or its use must be frequently alternated with the cutting or cauterizing device.

To alleviate the requirement for multiple instruments, it is known to provide combination irrigators/scalpels. For example, U.S. Pat. No. 4,642,090 to Utrata describes a hollow scalpel handle through which fluid can flow to wash the cutting edge of a scalpel blade affixed to the scalpel handle. Although this device provides limited irrigation, the surgeon is unable to aspirate bodily tissue cut by the scalpel. In addition, the fixed position of the scalpel blade greatly limits the type of operation for which this device is suited. Generally, only well exposed tissues such as the eye can be operated on using this device. Insertion of the protruding scalpel through narrow incisions or bodily cavities risks damaging healthy tissue by inadvertent cutting.

Accordingly, to alleviate problems associated with surgical devices known in the prior art, it is an object of the present invention to provide a lavage having a fluid passageway through which irrigation fluid can pass to a desired surgical operating site, and through which tissue debris derived from the operating site can be removed by aspiration.

Another object of the present invention is to provide a lavage having a cutting or cauterizing tip that is not exposed until the tip is positioned at the desired operating site.

Yet another object of the present invention is to provide a handheld, disposable lavage with an irrigation-/aspiration cannula and a separate tool for cutting, grasping or cauterizing that fits inside the irrigation/aspiration cannula.

Another object of the present invention is to provide a handheld, disposable lavage with an irrigation/aspiration cannula and a separate tool for cutting, grasping or cauterizing over which a shield that can be reversibly retracted and extended from the irrigation/aspiration cannula to fit over the tool.

Still another object of the present invention is to provide a lavage having an irrigation/aspiration cannula through which liquid or solid movement is controlled by a rotary valve positioned in an attached valve body configured to be held in one hand with the thumb of that one hand acting to open or close the valve as desired.

Yet another object of the present invention is to provide a lavage having an irrigation/aspiration cannula through which extended objects can be introduced by passing through a breachable seal attached to a conduit piece in fluid communication with the irrigation/aspiration cannula.

Another object of the present invention is to provide a lavage having an irrigation/aspiration cannula coupled to a standard conduit piece having an attached breachable seal through which extended objects or fluids can be introduced, and through which liquid or solid movement is controlled by a valve positioned in an attached valve body that is configured to be held in one hand with the thumb of that one hand acting to open or close the valve as desired.

An additional object of the present invention is to provide a conduit piece having a longitudinally extending passageway in fluid communication with a longitudinally extending cannula so that streams of fluid or extended objects can be introduced into the cannula through the longitudinally extending passageway without suffering substantial deflection.

In accordance with the foregoing objectives, a surgical device that includes a first cannula formed to define a first interior channel is provided. A second cannula is positioned substantially within the first interior channel of the first cannula and acts to define a second interior channel. A conduit piece defining a first passageway in fluid communication with the first interior channel of the first cannula, a second passageway connected in fluid communication with the second cannula, and a third passageway connected in fluid communication with the first interior channel of the first cannula, is connected to the first cannula. The second passageway can be sealed with a breachable seal means that permits piercing insertion of tools or other surgical instruments. The entire device can be manually held using an elongated valve body coupled to the conduit piece and shaped to have a manually grippable longitudinally extending body. This longitudinally extending body defines a fourth passageway extending longitudinally therethrough which is connected in fluid communication to the third passageway of the conduit piece, with fluid flow within said fourth passageway being controlled by a manually operable rotary valve.

In one preferred embodiment, the second passageway is configured to lie in substantially coaxial relationship to the first passageway. Fluid under high pressure is forced through the second passageway and into the interior channel of the first or second cannula. This high pressure fluid can be used to efficiently dissect, cut, separate or move tissue. Alternatively, the second cannula can be formed to have an inner diameter sufficiently large to allow passage of an optic fiber capable of conveying a laser beam for laser cauterization of bodily tissue. In other embodiments of the invention the inner diameter of the second cannula is selected to allow insertion, passage through, and withdrawal of surgical instruments such as pincers, biopsy needles, probes, or graspers. Electrically insulated leads passing through an electrically insulated second cannula can be used for electrical cauterization in yet another preferred embodiment.

In other preferred embodiments a surgical instrument such as a knife, scissors, pincers, needles or probes can be mounted to either the first cannula or a rod situated at least partially within the first cannula. In certain embodiments, it is possible to provide a mechanism for retracting the surgical instrument from first cannula so that the instrument is shielded by the first cannula as the lavage is moved to or away from an operating site. When access to the surgical instrument is desired, an extension mechanism can be enabled to move the surgical instrument from it shielded position in the cannula to its normal operating position. For example, a cutting knife can be mounted on a movable rod substantially positioned with the first interior channel of the first cannula. The rod and the cutting knife mounted thereupon can be moved outward from a first position within the first interior channel of the first cannula by engaging an extending means for extending the cutting knife from the first position within the first interior channel of the first cannula to a second position extending at least partially from the first interior channel. The cutting knife can be retracted by way of a retracting means for retracting the cutting knife from the second position extending out from the first interior channel back to the first position within the first interior channel of the first cannula.

The surgical instrument can also be permanently mounted so that it remains immobile relative to the first cannula. For example, the cutting knife having a cutting edge can be permanently mounted to the first cannula so that its cutting edge extends outward into the first interior channel of the first cannula. The cannula is formed to define a notch or slot that at least partially exposes the cutting edge of the cutting knife. The cutting knife remains at least partially shielded by a shielding portion of the cannula adjacent to the notch defined within the first cannula.

In another preferred embodiment the surgical instrument is permanently mounted and shielding action is provided by a movable shield. For example, a surgical instrument such as the cutting knife can be mounted to first cannula so that the cutting edge protrudes from the first cannula. A shield, configured to be movable within the first interior channel of the first cannula, can be extended to shield the cutting edge of the cutting knife. This shield can also be retracted to expose the instrument when use of the instrument is desired. In certain embodiments, movement of the shield is only enabled upon release of a lock mechanism.

One advantage of the present invention is provided by the conjunction of a surgical instrument and means for providing irrigation/aspiration on the same handheld assembly. A surgeon can cut bodily tissue and simultaneously wash away blood flow resulting from the cut. The amount of saline irrigation that needs to be supplied can be determined and supplied by the surgeon himself, without necessarily requiring the assistance of other personnel. The time required for a surgical procedure can be diminished, and the need for auxiliary personnel to operate separate irrigation or aspiration devices can be eliminated.

Another advantage of the present invention is a consequence of the modular construction of the individual components of the disposable lavage. A standard conduit piece having a plurality of passageways extending therethrough can be fitted with a second cannula disposed within the first interior channel of the first cannula and attached in fluid communication with the conduit piece, an extension and retraction mechanism for extending or retracting a shield movable in the first interior channel of the first cannula, an extension and retraction mechanism for extending or retracting a surgical instrument movable in the first interior channel of the first cannula, a valve body having a passageway in fluid communication with the passageways of the conduit piece and wherein a rotary valve is positioned to control aspiration/irrigation, a breachable seal element having a membrane that can be pierced by a needle to inject fluids into the first cannula, or any combination of the preceding components as well as other components that can also be conjoined to form the lavage assembly. Each of these components can be inexpensively produced and mounted to the conduit piece, allowing a lavage unit to be disposable. This greatly reduces the problems associated with cleaning and sterilization associated with instruments designed for reuse.

Other objects, features and advantages of the present invention will become apparent with reference to the following drawings and description of certain embodiments of the invention.

BRIEF DESCRIPTION OF THE DRAWINGS

FIG. 11 is a partial side view, cutaway to show a device having a fixed cutting knife and a retractible shield for the knife;

FIG. 12 is a perspective view of the retractible shield shown in FIG. 11, with the shield being positioned to partially expose the knife;

FIG. 13 is an exploded view of a dual lock mechanism that can be threaded onto the conduit piece and is suitable for holding the shield in a predetermined position relative to the knife until both a first lock element and a second lock element are disabled;

FIG. 14 is a closeup side view of the dual lock mechanism in a released position to permit movement of the shield;

FIG. 15 is view of the dual lock mechanism of FIG. 14 in a locked position;

DETAILED DESCRIPTION OF THE DRAWINGS

Figure 1:
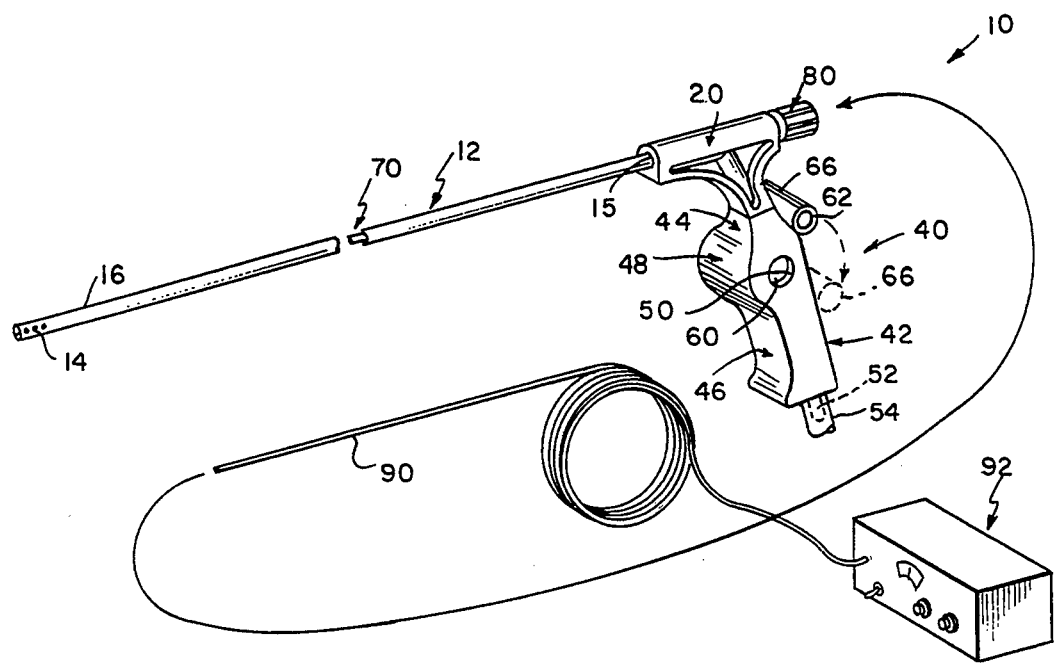
FIG. 1 is a perspective view of a disposable lavage having a central cannula through which an optic fiber capable of transmitting a laser beam can be inserted.
Figure 2:
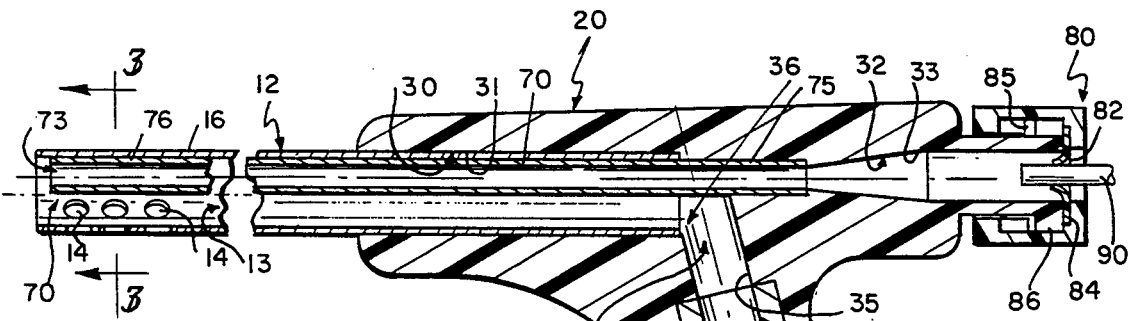
FIG. 2 is a side sectional view of the disposable lavage shown in FIG. 1, showing insertion of the optic fiber through a breachable seal.
Figure 3:
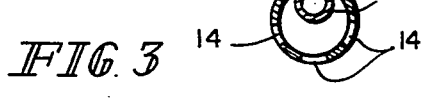
FIG. 3 is a cross sectional view along lines 3—3 of of the device shown in FIG. 2, showing the central cannula and the outer tube.

As illustrated in FIGS. 1-3, a disposable lavage 10 has a first cannula 12 defining a first channel 13 situated in fluid communication with a conduit piece 20. The first cannula 12 is attached to the conduit piece 20 at its attachment end 15. The first cannula 12 is positioned to longitudinally extend outward from the conduit piece 20 to terminate at a tip 16. A plurality of apertures 14 are defined by the first cannula 12 near the tip 16. The first cannula 12 is generally formed to have a tubular shape, and is constructed from inexpensive and rigid materials such as stainless steel or relatively rigid engineering-grade plastics such as polycarbonates.

As shown in the sectional view of FIG. 2, the conduit piece 20 is formed to define a first passageway 30 having first passageway walls 31, a second passageway 32 having second passageway walls 33, and a third passageway 34 having third passageway walls 35. The first, second and third passageways 30, 32, and 34 are generally tubular cavities through which fluid can flow. The passageways 30, 32, and 34 intersect each other at a branch 36 that is centrally positioned in the conduit piece 20. In the embodiment illustrated in FIG. 2, the first cannula 12 has its attachment end 15 inserted into the first passageway 30 to extend as far as the branch 36. The attachment end 15 is fixed in place by an adhesive (not shown) that holds the attachment end 15 in close contact with the first passageway walls 31. Of course, permanent attachment of the attachment end 15 of the first cannula 12 to the conduit piece 20 can also be provided by other means that can include friction couplings, locking tabs (not shown) that reciprocally engage the attachment end 15 to the conduit piece 20, nipples or threads extending from the conduit piece 20 (not shown) over which the attachment end 15 can be coupled to the conduit piece 20, or any other means for providing a secure connection between the conduit piece 20 and the first cannula 12.

Although metals such as stainless steel can be used to form the conduit piece 20, it is often advantageous to reduce costs and increase reliability by molding the conduit piece 20 as one piece. Rigid thermoset plastics such as polycarbonate or polyethylene are preferred molding plastics. The low cost of molded plastics allows the conduit piece to be disposable, eliminating costly maintenance and sterilization procedures associated with manufacture of non-disposable conduits. Construction of the conduit piece 20 from plastics rather than metals also has the advantage of permitting the conduit piece 20 to be formed completely or partially transparent, allowing an operator to visually determine if one of the passageways 30, 32, or 34 is completely or partially blocked by solid material.

Figure 16:
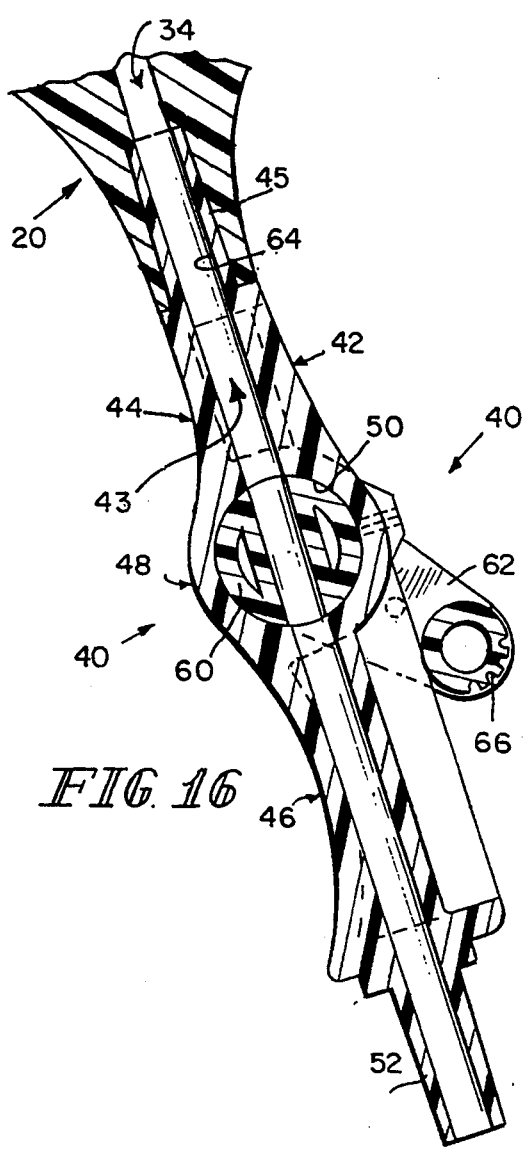
FIG. 16 is a transverse sectional view through a single passage valve incorporated in FIG. 1.

The third passageway 34 of the conduit piece 20 is placed in fluid communication with a valving mechanism 40 that is best shown in perspective view in FIGS. 1 and 16. The valving mechanism 40 includes a valve body 42 that is formed to define a neck 45 through which a fourth passageway 43 is situated in fluid communication with the third passageway 34. The conduit piece 20 is joined to the valve body 42 by insertion of the neck 45 into the third passageway 34 for frictional or adhesive coupling of the passageway wall 35 to the neck 45.

The valve body 42 is also configured to be manually grippable for ease of operation. The valve body 42 is formed to provide a forward bottom portion 44 shaped to be gripped by the index finger of one hand and a rearward bottom portion 46 shaped to be gripped by the middle finger and, depending upon the size of the hand, by the fourth finger of the hand, with a depending central portion 48 between the forward and rearward portions 44, 46. It will be appreciated from the sectional view of FIG. 1 and FIG. 16 that the recessed portions 44, 46 are smoothly transversely recessed for gripping comfort while the depending central portion 48 is smoothly rounded to fit between the index and middle fingers. It will further be appreciated that, in this description and in the appended claims, statements such as "engaged by the index finger" and "engaged by the middle finger" are intended to indicate the general shape and size of an adult's hand relative to the valve mechanism 40 and that the valve body 42 is proportioned and shaped to be held generally by the index and middle fingers pressing the body against the palm of the hand, leaving the thumb free for movement to control the mechanism.

The valve body 42 is further provided with a nipple 52 to which a fluid line 54 is attached. The fluid line 54 can be used to provide fluids to the fourth passageway 43 or to provide a passage through which fluids and solids can be withdrawn from the fourth passageway 43 by a vacuum (vacuum generating apparatus or fluid supply apparatus not shown). If desired, the valve body 42 may have, for instance, one, two or even three or more fluid lines connected in fluid communication with the fourth passageway 43 (FIG. 17, described hereinafter, shows a dual fluid line assembly).

The valve body 42 is molded to provide a cylindrical opening 50 extending transversely through the valve body and illustratively, just above the central body portion 48 which is held between the index and middle fingers of the hand. This cylindrical opening 50 is positioned to intercept the fourth passageway 43 extending through the valve body 42 as best seen in FIG. 2. A cylindrical, molded plastic, one-piece rotor 60 is snugly and slidably rotatably inserted in the cylindrical opening 50 to block the fourth passageway 43 except when the rotor 60 is in its passageway opening position as shown in FIG. 16.

The valve body 42 may preferably be molded from a rigid material such as a polycarbonate plastic while rotor 60 may preferably be molded from a softer plastic such as a polypropylene, nylon or teflon. The closeness of the snug fit of the rotor 60 in the cylindrical opening 50 and the nature of the material from which the valve body 42 and rotor 60 are molded will determine the pressure capacity of the valving mechanism. It will be appreciated that a very snug rotor 60 fit in the cylindrical opening 50 will accommodate high pressure. The rotor 60 is provided with a peripherally extending thumb engaging arm 62 integrally molded thereon. The thumb engaging arm 62 extends generally parallel to and above the rotor 60. This engaging portion 62 may be serrated as indicated at 66 to provide a gripping surface for the thumb.

In FIG. 2, the illustrative rotor 60 is formed to define a passageway 64 which is substantially in alignment with the fourth passageway 43. When the rotor 60 is rotated by movement of the thumb engaging arm 62, however, the passageway 43 will be blocked by the rotor 60. This is illustrated in FIG. 1, in which the engaging arm 62, initially in a forward position with the passageway 64 in substantial alignment and in fluid communication with the fourth passageway 43 is reversibly moved to a closed position in which the fourth passageway is blocked by the rotor 60. In the closed position there is no fluid communication between fluid lines and the third passageway 34 of the conduit piece 20.

The present invention, therefore, provides a two-piece, disposable, plastic stopcock handle-valve or valving mechanism which can be held and operated by either hand. The body of the handle-valve has a contoured bottom surface that fits into enough of the palm side of either hand of the operator, starting with the index finger, to permit the operator to both operate the handle-valve and direct its motion. Importantly, for control purposes, the thumb engages an actuating means which is preferably disposed axially and longitudinally just above the rotor of the valve, and this actuating or engaging portion may be integrally molded with the rotor. For control purposes, the arm 62 connected to the rotor 60 should have a moment-arm of approximately one inch and a stroke of approximately three-fourths inch, a comfortable span for either an adult female or male hand. The top extension of the thumb engaging portion may be serrated to facilitate its movement by the thumb and the bottom or other surfaces of the valve body may be serrated at convenient locations to provide a convenient and comfortable grip. The valve body 42 and the rotor 60 are assembled with a slight interference fit to provide a good seal between the body and the rotor 60 without requiring extreme pressure in excess of that which is comfortable for an adult female or male to move by thumb action.

Figure 17:
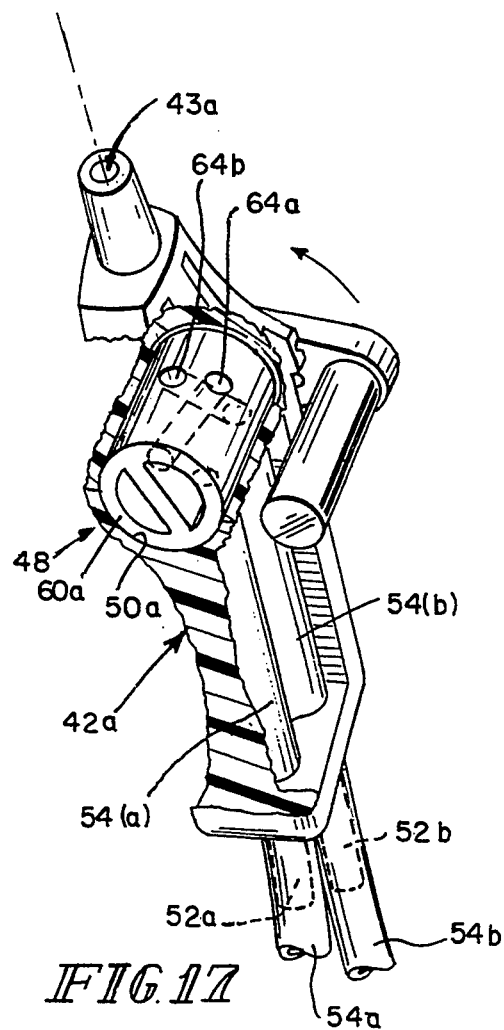
FIG. 17 is a perspective view with portions broken away of a modification of the valve in FIG. 16 wherein a duel input and a single output is illustrated.

Another embodiment of a valve body having dual fluid line input/ouput is shown in FIG. 17. A valve body 42a is formed to have two input nipples 52a and 52b that allow respective connection to fluid lines 54a and 54b. These fluid lines 54a and 54b can alternatively be used to provide fluids to a fourth passageway 43a (for example through line 54a) or to provide a passage through which fluids and solids can be withdrawn from the fourth passageway 43a by a vacuum (for example through line 54b; vacuum generating apparatus or fluid supply apparatus not shown). The valve body 42a is molded to provide a cylindrical opening 50a extending transversely through the valve body 42a. This cylindrical opening 50a is positioned to intercept the fourth passageway 43a and the valve body 42a. A cylindrical, molded plastic, one-piece rotor 60a is snugly and slidably rotatably inserted in the cylindrical opening 50a to block the fourth passageway 43a except when the rotor 60a is in one of its two passageway opening positions such that a passageway 64a is in fluid communication between fluid lines 54a and passageway 43a, or alternatively such that passageway 64b is in fluid communication between fluid lines 54b and 43a. Coupling of the valve body 42a to a conduit piece 20 and cannula 12 gives a surgeon the ability to rapidly alternate between irrigation and aspiration of a surgical site by simply rotating the rotor 60a to the appropriate position for introduction or withdrawal of fluids.

Figure 4:
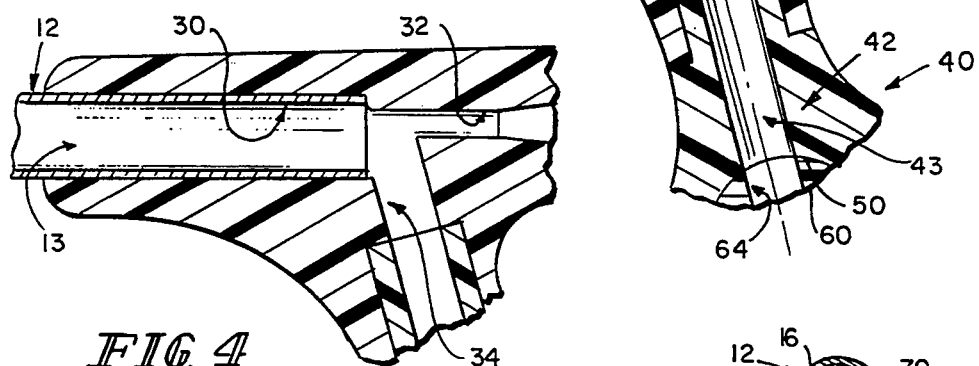
FIG. 4 is a partial side sectional view of another embodiment of a disposable lavage constructed without a central cannula.

Introduction or withdrawal of fluids does not necessarily have to be accomplished solely through the fluid line 54 (or 54a or 54b) by way of the fourth passageway 43 (or 43a) and the third passageway 34. As shown in FIGS. 2 and 4, fluids and solids can be withdrawn from or introduced to pass through the first passageway 30 defined in the conduit piece 20 by way of the second passageway 32. The second passageway 32 is defined by the second passageway walls 33 of the conduit piece 20 and is configured to lie in substantially coaxial relationship to the first passageway 30. This geometry permits longitudinally extending objects introduced through the second passageway 32 to easily pass into the the first passageway 30 without substantial deformation or bending. Also, as best shown in FIG. 4, the alignment of the first and second passageways 30 and 32 permits longitudinally extending streams of fluid under high pressure to be introduced through the second passageway 32 to pass through the first passageway 30, and from that passageway 32 into the first cannula 12. Such fluid would not be substantially slowed or redirected during its passage, and could accordingly be utilized to provide a stream of water capable of cutting or moving bodily tissue as desired.

The second passageway 32 can also accomodate a second cannula 70 defining a second channel 73 with which the second passageway 32 is connected in fluid communication (best shown in FIG. 2). The second cannula 70 is attached to the conduit piece 20 at its attachment end 75. The second cannula 75 is positioned to longitudinally extend outward from the conduit piece 20 to terminate at a tip 76. The second cannula 70 is dimensioned to fit within the first cannula 12, and like the first cannula 12 is generally formed to have a tubular shape. The position of the second cannula 70 relative to the first cannula 12 is again indicated in cross section in FIG. 3. The tip 76 can also be arranged to float within the first cannula 12, to be held in fixed attachment to the first cannula 12 by an adhesive or spot welding, or can be arranged to lie concentrically within the first cannula 12. Like the first cannula 12, the second cannula 70 can also be constructed from inexpensive and rigid materials such as stainless steel or relatively rigid engineering-grade plastics such as polycarbonates.

In the embodiment illustrated in FIG. 2, the second cannula 70 has its attachment end 75 inserted to extend through both the first passageway 30 and the branch 36 partially into the second passageway 32, where it is fixed in place by an adhesive (not shown) that holds the attachment end 75 in close contact with the second passageway walls 33. Permanent attachment of the attachment end 75 of the second cannula 70 to the conduit piece 20 can also be provided by other means that can include frictive couplings, locking tabs (not shown) that reciprocally engage the attachment end 75 to the conduit piece 20, nipples or screw threads extending from the conduit piece 20 (not shown) over which the attachment end 75 can be coupled to the conduit piece 20, or any other means for providing a secure connection between the conduit piece 20 and the second cannula 70.

Fluid flow into or out of the second passageway 32 can be controlled by a seal 80 that blocks the second passageway 32. In the embodiment shown in FIGS. 1 and 2 the seal 80 includes a membrane 82 conformably stretched to fit over a seal body 84. The membrane 82 can be composed of an elastomeric material that permits pierceable entry of objects and still provides sealing action to limit backflow of fluid out of the second passageway 32. The seal body 84 is formed to have threads 85 capable of engaging corresponding threads 86 formed in the conduit piece 20 to provide screw lockable engagement between the seal 80 and the conduit piece 20. Objects contemplated for insertion into the second passageway 32 through the seal 80 include but are not limited to hypodermic needles, auxiliary cannula, surgical instruments such as scissors, pincers, graspers, or probes, optical fibers to assist in illuminating or imaging a dimly lit or visually inaccessible surgical site, or as shown in FIG. 1 and 2 an optical fiber 90 coupled to laser 92. The optical fiber 90 could be used to deliver to a desired area the coherent laser energy produced by the laser 92 to cauterize selected bodily tissue. In the disclosed embodiment, control of the optic fiber 90 is enhanced because the fiber 90 is tightly held in a desired position by the second cannula 70.

Figure 18:
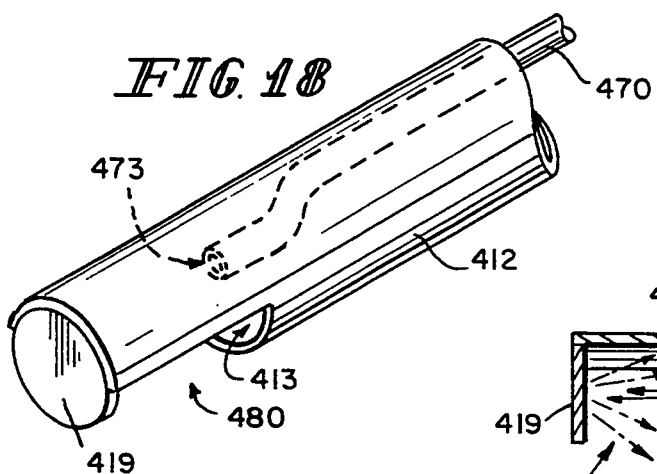
FIG. 18 is a perspective view of an end portion of a disposable lavage having a cannula with the second cannual positioned adjacent a shield for high pressure fluid cutting.
Figure 19:
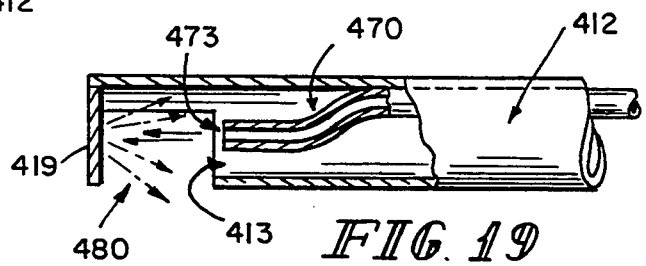
FIG. 19 is a side elevation of FIG. 18 with portions broken away to show the cutting region.

In addition to its uses as an instrument conduit, the second cannula 70 can be used to channel high pressure fluids to an operating site (not shown). This is best seen in the embodiment of the invention illustrated in FIGS. 18 and 19. In FIGS. 18 and 19, a second cannula 470 (similar to the second cannula 70) can be configured to operate in conjunction with a high pressure fluid source (not shown) to provide tissue cutting action. The second cannula 470 is positioned within a cavity 413 defined by a first cannula 412, and is held in place by fixed attachment to the conduit piece 20. The first cannula 412 is formed to have a terminal shield 419 that is positioned to intercept and dissipate high pressure fluid streaming from the channel 473 of the second cannula 470. In operation, tissue (not shown) can be placed in a cutting region 480 located between the terminal shield 419 and the channel 473 of the second cannula 470. High pressure fluid (flow direction indicated by arrows in FIG. 19) moving at high velocities in the cutting region 480 will slice tissue as desired.

Figure 5:
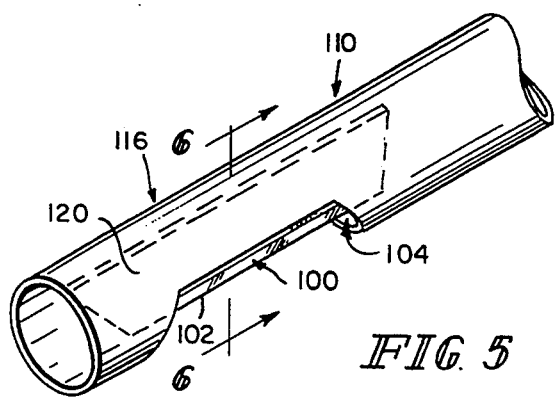
FIG. 5 is a perspective view of a disposable lavage tip having a permanently mounted cutting knife, with the knife being accessible only in the notch region and the cannula providing a partial shield.
Figure 6:
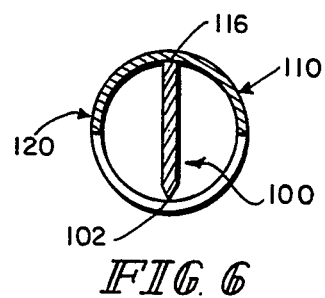
FIG. 6 is a cross sectional view taken along line 6—6 showing the mounted cutting knife.

In certain embodiments of the invention a knife 100 such as indicated in FIGS. 5 and 6 can be mounted at a tip 116 of the cannula 110. Access to the cutting edge 102 of the knife 100 is permitted by forming the tip 116 with a notch 104 that partially exposes the cutting edge 102. The remainder of the tip 116 acts as a partial shield 120 that redirects tissue as the tip 116 is moved through a body (not shown).

Figure 7:
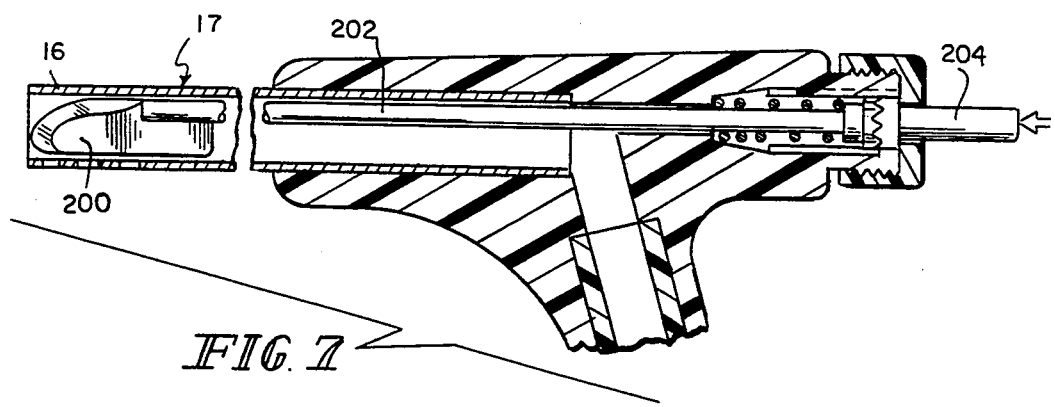
FIG. 7 is a side sectional view of a disposable lavage having a retractible knife connected to a thumb actuated button which is depressed to extend the knife.
Figure 8:
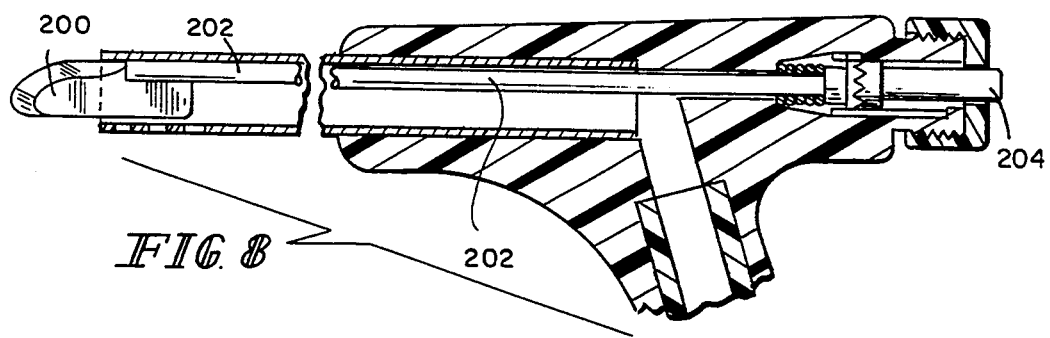
FIG. 8 shows the device of FIG. 7 with the knife extended from the outer tube and the button in a depressed position.

A knife 200 can also be mounted to a movable element 202 situated with the cannula 12 such as shown in FIGS. 7 through 10. As shown in FIG. 7 the knife 200 normally rests in a home position within the cannula 12. A trigger button 204 can be pushed inward, causing the rod 202 and connected knife 200 to extend out of the cannula 12. The rod 202 and attached knife remain in the extended position until the button 204 is redepressed.

Figures 9, 10:
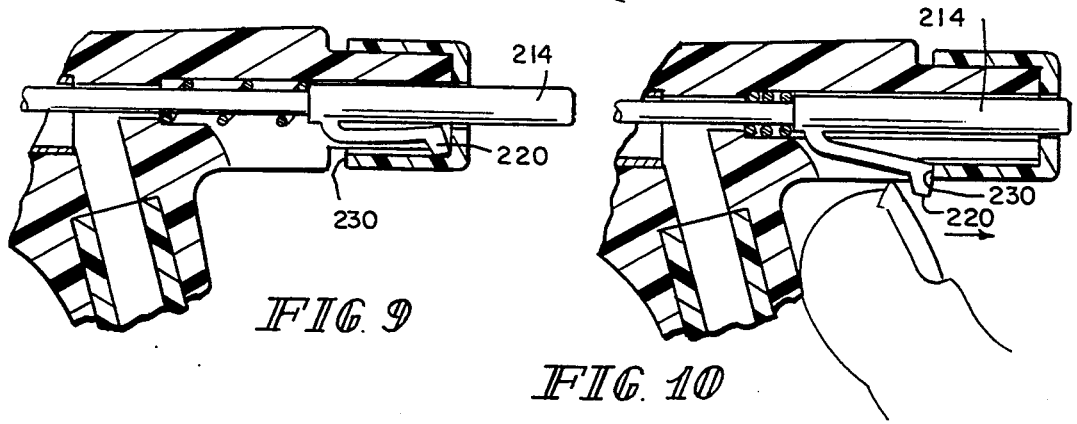
FIG. 9 is a side sectional view showing an alternative embodiment of the button having a thumb actuated indicator/catch for holding the knife in an extended position.
FIG. 10 shows the device of FIG. 9 with the indicator/catch engaged to hold the knife in an extended position and provide tactile indication that the knife is in the extended position.

Alternative assemblies providing locking extension of the knife 200 from the cannula 12 are shown in FIGS. 9 and 10. A flexible lever 220 is shown in its home position in FIG. 9. When a trigger button 214 is inwardly depressed, the flexible lever 220 moves outward. Retraction of the knife 200 is prevented because the lever 220 engages a catch 230 that prevents reverse motion of the lever 220 and the attached rod 202. Release of the catch 230 by inwardly pushing the lever 220 to clear the catch 230 enables the retraction of the knife 200.

As shown in FIGS. 11 through 15, a shield 300 can be alternately extended or retracted from the cannula 12 to respectively cover or uncover a knife 200 mounted to the cannula 12. The knife 200 is mounted to the cannula 12 so that it protrudes from the tip 16 of the cannula 12 in a position suitable for surgical operations. As best shown in FIG. 12, the shield 300 is split to form a channel 302 which slides over the permanently mounted knife 200. In the illustrated embodiment the shield 300 is concentrically arranged within the cannula 12, and is formed to have a generally tubular shape with a circular cross section and an outer diameter slightly smaller than an inner diameter of the cannula 12. It is contemplated that a shield can also be formed to have arcuate, elliptical, polygonal or other type cross section as desired.

In the embodiment shown in FIGS. 11-15 the extension and retraction of the shield 300 is facilitated by the use of a dual lock assembly 310 that holds the shield in a desired position relative to the knife 200. The dual lock assembly 310 is threadingly attached to the conduit piece 20 so that it lies substantially colinear to the longitudinally extending cannula 12. The dual lock assembly 310 is best seen in the exploded perspective view of FIG. 13, which respectively illustrates from left to right a rod 315 that couples the dual lock assembly 310 to the shield 00, a housing 320, a first lock element 330, and a second lock element 340.

The housing 320 is formed to have a housing cavity 321 that extends therethrough. Threads 317 are defined in the housing 320 to allow threaded engagement with the conduit piece 20. In other embodiments (not shown), locking tabs and adhesive or frictional couplings can also be used to join the housing 320 of the dual lock assembly 310 to the conduit piece 20. The housing 320 is also formed to have a "D"-shaped aperture 311 (generally indicated in FIGS. 11, 14–15) allowing access to the cavity 321. The housing 320 is also formed to have a land 322. The land 322 is a generally flattened region of the housing 320 through which a latch channel 326 is defined to extend. The latch channel 326 communicates with a plurality of side channels 324 formed in the housing 320 to extend perpendicular to the latch channel 326. Between each pair of side channels 324 the housing 320 acts to form stops 325. It will be appreciated that these channels 324 and 326 can be cut or formed during mold casting of the housing 320 as desired.

The first lock element 330 includes a plug 332, a flexible arm 333, a tongue 334, and a button 336 having a shield retraction pad 338 and a shield extension pad 339. As best shown in FIGS. 11, 14, and 15, the plug 332 can slidably reciprocate in the cavity 321 Of the housing 320. The plug 332 interconnects the rod 315 and the combination of the flexible arm 334 and the button 336. When the dual lock assembly 310 is fully assembled, the button 336 can be positioned to slidably move along the land 322 of the housing 320, pulling (or pushing, as appropriate) the plug 332 and the connected rod 315.

The second lock element 340 includes a shaft 341 connected to a handle 346. The shaft 341 has a flat land 342 and a curved land 344, giving it a generally "D"-shaped cross section that is dimensioned to fit through the "D"-shaped aperture 311 opening into the housing 320. Because of this "D"-shape, the shaft 341 cannot rotate relative to the housing 320. Situated opposite the handle 346, an end 343 of the shaft 341 is formed to define cross cutting channels 348 and 349. As best seen in FIGS. 11 and 14–15, the end 343 of the shaft 341 has a generally circular cross section (with a channel 349 passing through it) and is dimensioned to conformably ride in the cavity 321 in the housing 320. Because of the flattened land 342, the remainder of the shaft 341 does not completely fill the cavity 321.

When the dual lock assembly 310 is assembled and positioned so that the first lock element 330 and the second lock element 340 are fully engaged in locking position (as seen in FIG. 15), it is impossible to either extend or retract the shield 300. If either the the shield retraction pad 338 or the shield extension pad 339 is downwardly pushed, the consequent downward movement of the flexible arm 333 is stopped as the tongue 334 contacts the land 342 of the shaft 341. As a result, longitudinal movement of the first locking element 330 is inhibited because the tongue 334 engages stops 325 formed in the housing 320.

As shown in FIG. 14, to unlock the first lock element 330 for either extension or retraction of the shield 300 requires that the handle 346 of the second lock element 340 be pulled outward from the housing 320 far enough so that the tongue 334 appended to the flexible arm 333 is situated over the channel 348. As indicated in FIG. 14, the positioning of the second lock element 340 in this disabled condition is indicated by the exposure of a red color 345 on the shaft 341. When the red color 345 is visible, either the second locking element 340 is not in a position to prevent unlocking of the first locking element 330 or the cutting knife 200 is completely or partially exposed, or both.

After the second locking element 340 has been disabled, the first locking element 330 can be moved to either a position suitable for extending or retracting the shield 300 simply by downwardly pushing either the shield retraction pad 338 or the shield extension pad 339 in the direction of the arrow. The flexible arm 333 flexes downward as the button 336 is depressed, forcing the tongue 334 into the channel 348. The shield can be retracted to fully or partially expose the knife 200 by applying sufficient downward force to the retraction tab 338 of the button 336 to keep the tongue 334 in the channel 348 and by simultaneously pressing the button 336 in the direction of the handle 346. After the shield 300 has been retracted a desired amount, the button 336 is released, allowing the flexible arm 333 to move back to its normal resting position and placing the tongue 334 in a locked position between the stops 325, such as shown for example in FIG. 15. By reversing this procedure the shield 300 can be moved to more fully or completely cover the knife 200. Extending the shield 300 requires applying sufficient downward force to the extension tab 339 of the button 336 to keep the tongue 334 in the channel 348 and simultaneously pressing the button 336 in the direction of the conduit piece 20. After the shield 300 has been extended a desired amount, the button 336 is released, allowing the flexible arm 333 to move back to its normal resting position and placing the tongue 334 in a locked position between the stops 325, such as shown for example in FIG. 11.

What is claimed is:

1. A surgical device comprising
   a first cannula formed to define a first interior channel, wherein said first cannula has first and second ends,
   a surgical knife positioned to protrude from the first end of the first cannula,
   means for shielding the surgical knife, and
   means for extending the shielding means from the first interior channel of the first cannula to shield the surgical knife and for retracting the shielding means into the first interior channel to expose the surgical knife.

2. The surgical device of claim 1, wherein the shielding means includes a second cannula positioned to move between a first position wherein the second cannula protrudes from the first end of the first cannula to shield the surgical knife and a second position wherein the second cannula lies substantially within the first interior channel of the first cannula to expose the surgical knife.

3. The surgical device of claim 2, wherein the surgical knife is mounted on the first cannula.

4. The surgical device of claim 1, wherein the extending and retracting means includes means for locking the shielding means in a predetermined position.

5. The surgical device of claim 4, wherein the locking means includes a first lock positioned to move between a first locking position that holds the shielding means in a predetermined position and a first lock release position that permits movement of the shielding means away from the predetermined position.

6. The surgical device of claim 4, wherein the surgical instrument is fixedly attached to the first cannula.

7. The surgical device of claim 5, wherein the surgical knife is fixedly attached to the first cannula.

8. A surgical device comprising
   a first cannula formed to define a first interior channel, wherein said first cannula has first and second ends,
   an instrument positioned to protrude from the first end of the first cannula means for shielding the instrument,
   means for extending the shielding means from the first interior channel of the first cannula, and
   for retracting the shielding means into the first interior channel to expose the instrument,
   wherein the extending and retracting means includes means for locking the shielding means in a predetermined position,
   wherein the locking means includes a first lock positioned to move between a first locking position that holds the shielding means in a predetermined position and a first lock release position that permits movement of the shielding means away from the predetermined position, and wherein the locking means includes a second lock positioned to move between a second lock locking position that prevents movement of the first lock from said first lock locking position to the first lock release position and a second lock release position that permits the first lock to be moved into the first lock release position.

9. The surgical device of claim 8, wherein the second lock is provided with coded indicia to indicate the position of the shielding means relative to the instrument.

10. The surgical device of claim 9, wherein the surgical instrument is fixedly attached to the first cannula.

11. The surgical device of claim 8, wherein the surgical instrument is fixedly attached to the first cannula.

12. A disposable lavage capable of carrying a surgical instrument comprising a first cannula formed to define a first interior channel, wherein said first cannula has first and second ends, means for mounting the instrument so that the instrument is positioned to protrude from the first end of the first cannula, means for shielding the instrument, means for extending the shielding means to shield the instrument and for retracting the shielding means to expose the instrument, and a conduit piece defining a first passageway into which the first cannula is inserted, a second passageway in fluid communication with the first interior channel of the first cannula, and a third passageway in fluid communication with the first interior channel of the first cannula.

13. The disposable lavage of claim 12, wherein the shielding means includes a second cannula formed to define a second interior channel, wherein said second cannula is positioned to move between a first position wherein the second cannula protrudes form the first end of the first cannula to shield the instrument and a second position wherein the second cannula lies substantially within the first interior channel of the first cannula to expose the instrument.

14. The disposable lavage of claim 13 wherein the instrument is mounted on the first cannula.

15. The apparatus of claim 14 wherein the instrument is a surgical knife.

16. The disposable lavage of claim 12, wherein the extending and retracting means includes means for locking the shielding means in a predetermined position.

17. The disposable lavage of claim 16, wherein the surgical instrument is fixedly attached to the first cannula.

18. The disposable lavage of claim 12, wherein the surgical instrument is fixedly attached to the first cannula.

19. The disposable lavage of claim 12, wherein when the shielding means is retracted, it is retracted into the interior of the first channel.

20. An aspirating and suction disposable lavage capable of carrying a surgical instrument comprising a first cannula formed to define a first interior channel, wherein said first cannula has first and second ends, means for mounting the instrument so that the instrument is positioned to protrude from the first end of the first cannula, means for shielding the instrument, means for extending the shielding means to shield the instrument, and for retracting the shielding means to expose the instrument, a conduit piece defining a first passageway attached in fluid communication with the first interior channel of the first cannula for connecting the said first interior channel to an aspiration source and a suction source, and valve means for controlling fluid flow through the first passageway for the introduction of and removal of fluid to and from the interior channel.

21. The lavage of claim 20, wherein the shielding means includes a second cannula formed to define a second interior channel, wherein said second cannula is positioned to move between a first position wherein the second cannula protrudes from the first end of the first cannula to shield the instrument and a second position wherein the second cannula lies substantially within the first interior channel of the first cannula to expose the instrument.

22. The disposable lavage of claim 21, wherein the surgical instrument is fixedly attached to the first cannula.

23. The lavage of claim 20, wherein the extending and retracting means includes means for locking the shielding means in a predetermined position.

24. The lavage of claim 20, wherein when the shielding means is retracted, it is retracted into the first channel.

25. The disposable lavage of claim 24, wherein the surgical instrument is fixedly attached to the first cannula.

26. The disposable lavage of claim 25, wherein the cannula is positioned in a patient by an operator by hand gripping a hand gripping surface on the conduit piece to move the conduit piece and cannula to accurately position the instrument in a patient's body.

27. The lavage of claim 25, wherein the valve means has a valve body and a hand gripping surface is on the valve body.

28. The disposable lavage of claim 20, wherein the surgical instrument is fixedly attached to the first cannula.

29. The disposable lavage of claim 20, wherein the valve means is rigidly attached to the conduit piece.

30. The lavage of claim 29, wherein the valve means has a valve body and the hand gripping surface is on the valve body.

31. The lavage of claim 30, wherein digits on the hand holding the conduit piece can operate the valve means as the instrument is being positioned in the patient.

32. The lavage of claim 29, wherein digits on the hand holding the conduit piece can operate the valve means as the instrument is being positioned in the patient.

33. The disposable lavage of claim 20, wherein the cannula is positioned in a patient by an operator by hand gripping a hand gripping surface on the conduit piece to move the conduit piece and cannula to accurately position the instrument in a patient's body.

34. The lavage of claim 33, wherein the valve means has a valve body and the hand gripping surface is on the valve body.

35. The lavage of claim 33, wherein digits on the hand holding the conduit piece can operate the valve means as the instrument is being positioned in the patient.

36. The lavage of claim 20, wherein the valve means has a valve body and a hand gripping surface is on the valve body.

* * * * *